(12) United States Patent
Lamy et al.

(10) Patent No.: US 7,776,367 B2
(45) Date of Patent: Aug. 17, 2010

(54) **USE IN THE COSMETICS FIELD OF AN EXTRACT OF AN EXSUDATE OF THE PLANT *DANIELLA OLIVERI*, IN PARTICULAR AS AN ANTIWRINKLE AGENT**

(75) Inventors: Cécile Lamy, Orleans (FR); Nancy Sauvan, Meudon (FR); Isabelle Renimel, Trainou (FR); Patrice Andre, Neuville aux Bois (FR); Sylvie Darnault, Orleans (FR)

(73) Assignee: LVMH Recherche, Saint Jean de Braye (FR)

( * ) Notice: Subject to any disclaimer, the term of this patent is extended or adjusted under 35 U.S.C. 154(b) by 63 days.

(21) Appl. No.: 12/217,230

(22) Filed: Jul. 2, 2008

(65) Prior Publication Data
US 2009/0274779 A1 Nov. 5, 2009

(30) Foreign Application Priority Data
Apr. 30, 2008 (FR) .................. 08 52930

(51) Int. Cl.
*A61K 36/00* (2006.01)
*A61K 9/00* (2006.01)
*A61K 47/00* (2006.01)

(52) U.S. Cl. .................. 424/725; 424/775; 424/400; 424/439

(58) Field of Classification Search .................. None
See application file for complete search history.

(56) References Cited
FOREIGN PATENT DOCUMENTS
EP 1 442 736 A 8/2004
FR 2 890 312 A 3/2007

OTHER PUBLICATIONS

Ahmadu et al. (Phytochemical and antimicrobial activities of the *Daniellia oliveri* leaves, Fitoterapia 75 (2004), 729-732).*
XP002510693 Database MEDLINE Onwukaeme, N. et al. "Effects of *Daniellia oliveri* stem bark and leaf extracts on rat skeletal muscle", Phytotherapy Research, vol. 13, No. 5, Aug. 1999, pp. 419-421. Abstract and full article.
XP002510694 Database EMBASE Onwukaeme, N. "Pharmacological activities of extracts of *Daniellia oliveri* (Rolfe) Hutch. And Dalz. (Leguminosae)", Phytotherapy Research, vol. 9, No. 4, 1995. Abstract Only.
XP 002510318 Database BIOSIS, Jegede, I. et al. "Micromorphological, anti-nociceptive and anti-inflammatory investigations of stem bark of *Daniellia oliveri*", African Journal of Biotechnology, vol. 5, No. 10, May 2006. Abstract Only.

* cited by examiner

*Primary Examiner*—Christopher R Tate
*Assistant Examiner*—Randall Winston

(57) ABSTRACT

The invention relates to the use, in a cosmetic composition or for the production of a cosmetic composition, of an extract of an exudate of the plant *Daniellia oliveri*, said exudate being at least partially made up of the oleoresin of said plant.

It relates most particularly to the use of this extract as a cosmetic agent for modifying the surface of the skin by giving it a smoother appearance through a reduction in the depth of the wrinkles and/or fine lines and/or by providing it with a re-plumping effect.

It also relates to a cosmetic care method for modifying the surface of the skin by giving it a smoother appearance through a reduction in the depth of the wrinkles and fine lines and/or by providing it with a re-plumping effect, comprising the application, to the areas of the skin in question, of a cosmetic composition containing this extract.

12 Claims, No Drawings

USE IN THE COSMETICS FIELD OF AN EXTRACT OF AN EXSUDATE OF THE PLANT *DANIELLA OLIVERI*, IN PARTICULAR AS AN ANTIWRINKLE AGENT

The present invention relates to the cosmetics field.

More specifically, the invention relates to the use in the cosmetics field of the plant *Daniellia oliveri*, and more specifically of an extract obtained from a natural exudate of this plant.

It relates more particularly to the use in the cosmetics field of extracts of such an exudate in cosmetic compositions or for the preparation of cosmetic compositions intended to modify the surface of the skin by giving it a smooth appearance through a reduction in the depth of the wrinkles and/or fine lines by providing it with a re-plumping effect.

Trees of the *Daniellia* genus are distributed geographically in tropical Africa. *Daniellia oliveri* is mainly found in West Africa (Burkina Faso, Ivory Coast, Nigeria, etc.). It is one of the species of the Sudanese and Guinean savannas.

The *Daniellia* genus, which belongs to the family Fabaceae or Leguminosae, is also known by other botanical synonyms such as Cyanothyrsus Harms or Paradaniellia Rolfe.

The *Daniellia oliveri* species is also known under the botanical name *Daniellia oliveri* (Rolfe) Hutch & Dalziel.

This species is also known by other botanical synonyms, in particular *Paradaniellia oliveri* Rolfe.

This plant is also known under the name Faro or *Daniellia* when it is desired to denote an essence of wood of species with the *Daniellia* genus, considered to be tropical essences.

*Daniellia oliveri* is a relatively tall, slender tree with a spread out top, reaching 15 to 20 m in height. Its leaves are pink to red at the time of flowering and its scaly bark is gray with a white-striped deep red slash. The trunk naturally secretes an exudate in the form of an oleoresin. The production can be amplified by natural phenomena, for instance attacks by parasites such as caterpillars which degrade the bark, or else on the occasion of bush fires. A mixture of bark in the form of sawdust and of oleoresin is generally found at the bottom of the tree.

The *Daniellia oliveri* species is traditionally used for various medicinal applications:

In Burkina Faso, the leaves are part of the treatment for malaria and white jaundice accompanied by liver problems. The bark is used to treat diarrheic diseases. The leafy stems are used against fatigue and pain during pregnancy. The oil extracted from the seeds is used for the treatment of skin conditions. The leaves at the base of which the flower develops, otherwise called bracts, can be used to treat coughs when they are chewed so as to swallow the juice therefrom.

The leaves (as a decoction) and the bark (as an infusion) are used as a diuretic and an aphrodisiac: the remedy is then applied to the body like a lotion. The powder of dried leaves is taken orally to treat yellow fever, a bad back and headaches, and can be applied to a wound.

Consequently, no use of the plant in the cosmetics field has been revealed in the literature, even less so as an antiwrinkle agent by virtue of a re-plumping effect.

It is precisely uses of this type which form the subject of the present invention.

In fact, the inventors of the present invention have now discovered, surprisingly and unexpectedly, that extracts of exudates of the plant *Daniellia oliveri*, and more specifically extracts containing oleoresin from this plant, have an antiwrinkle activity and can be used as a cosmetic agent for improving the surface appearance of the skin, in particular for reducing the depth of wrinkles and causing fine lines to disappear.

They have also been able to demonstrate that this activity is, at least in part, linked to a stimulatory activity on the internal lipogenesis of adipocytes or pre-adipocytes. This is reflected by an increase in the cell volume of the latter, resulting in better contact with the extracellular protein network. The dermis is thus re-plumped due to slight swelling, which makes it possible to reduce the depth of the wrinkles and fine lines and, consequently, to make them less apparent.

The discovery of this activity has allowed the inventors to propose a particularly original solution for improving the surface appearance of the skin. This solution consists in applying, to the parts of the skin to be treated, an effective amount of an extract obtained from exudates of the plant *Daniellia oliveri*.

Continuing their research, the inventors of the present invention have also been able to demonstrate that the exudates contain cadalene, i.e. the 1,6-dimethyl-4-(1-methylethyl) naphthalene derivative of formula $C_{15}H_{18}$, and that this cadalene is at least in part responsible for the activity of the extracts.

They have also been able to improve the method of extraction, so as to enrich the extract in cadalene.

Thus, according to a first essential feature, the present invention relates to the use, in a cosmetic composition or for the production of a cosmetic composition, of an extract of an exudate of the plant *Daniellia oliveri*, said exudate being at least partially made up of the oleoresin of said plant.

According to a second essential feature, the invention relates to a cosmetic care method for modifying the surface of the skin by giving it a smoother appearance through a reduction in the depth of the wrinkles and fine lines and/or by providing it with a re-plumping effect, which comprises the application, to the areas of the skin in question, of a cosmetic composition containing the extract of exudate.

Other features and advantages of the invention will become apparent in the detailed description which follows and also in the exemplary embodiments.

In the subsequent text, the term "extract of the invention" denotes the extracts obtained from an exudate, itself at least partially made up of the oleoresin of the plant, and the term "compositions of the invention" denotes the cosmetic compositions containing the extract of the invention.

As emerges from what has been disclosed above, it is generally known that an exudate is naturally secreted by the trunk of the tree and that its production may be amplified by natural phenomena, such as attacks by parasites, in particular caterpillars which degrade the bark.

Thus, a mixture which contains both oleoresin and sawdust from wood and/or bark generally flows along the trunk. Such a mixture constitutes an exudate that is particularly preferred for implementing the method for preparing the extract of the invention.

The extract of exudate of the invention is used, as emerges from the examples which follow, as a cosmetic agent for modifying the surface of the skin by giving it a smoother appearance through a reduction in the depth of the wrinkles and/or fine lines and/or by providing it with a re-plumping effect, thus conferring antiwrinkle properties on the composition of the invention.

The extract of the invention is, particularly advantageously, obtained by treating the exudate by means of a method comprising at least one extraction step with an apolar solvent.

A broad range of solvents may be used. However, referring to the classification of solvents by polarity as published by Veronika R. Meyer in Practical High-Performance Liquid Chromatography (1988), John Wiley and Sons, p. 120-121, solvents or mixtures of solvents for which the polarity parameter P' is between −2 and 0.2 will preferably be chosen.

This apolar solvent is advantageously chosen from the group comprising fluoroalkanes and derivatives thereof, such as methoxynonafluorobutane, ethoxynonafluorobutane, or 1,1,1,3,3-pentafluorobutane, cyclohexane, cycloheptane, heptane, isoheptane, hexane and pentane, and mixtures thereof.

According to a particularly advantageous variant of the invention, $CO_2$ in the supercritical state is used as apolar solvent.

It was found to be particularly advantageous to use the apolar solvent, in particular the $CO_2$ in the supercritical state, in the presence of an agent for modifying the polarity of said apolar solvent. This polarity-modifying agent is advantageously chosen from polar solvents. Methanol, ethanol or an ethanol/water mixture will preferably be used.

In general, the solvent used as polarity-modifying agent will be present in low proportions relative to the apolar extraction agent which constitutes the principal solvent medium. This modifying agent will generally be included in proportions of from 0 to 10%, preferably from 0 to 3%, by weight relative to the apolar solvent.

As disclosed above, the tests carried out by the inventors of the present invention have made it possible to demonstrate that cadalene is mainly responsible for the activity of the extracts of the invention.

This new discovery constitutes an invention in itself since the inventors of the present application have been able to demonstrate completely unexpected properties of cadalene. The latter in fact makes it possible to stimulate adipocytes or pre-adipocytes lipogenesis, making it possible to increase their cell volume and to produce, as disclosed above, a reduction in the depth of wrinkles and fine lines and, consequently, to render them less apparent.

Thus, the inventors of the present invention have been able to demonstrate a new application of cadalene and of extracts of plants containing cadalene, as an anti-skin ageing agent, in particular for reducing the depth of wrinkles and fine lines.

Among the extracts of the invention, those which contain cadalene will preferably be chosen.

A method of extraction which makes it possible to enrich the final extract of cadalene will preferably be used. This will be possible in particular by treating the extract obtained after the treatment of the exudate with an apolar solvent, where appropriate in the presence of a polarity-modifying solvent, by means of a flash chromatography technique and/or a high performance liquid chromatography (HPLC) technique.

The cosmetic composition of the invention advantageously contains from 0.01% to 5%, better still between 0.1% and 1% by weight of said dry extract.

The cosmetic composition of the invention may be formulated in various forms compatible with topical application and may in particular be in the form of a lotion, a milk, a gel, a cream or a stick, in particular for around the lips.

Finally, the cosmetic composition of the invention may also contain a product that acts on fibronectin synthesis, such as a galactolipid, in particular a galactosylglyceride, and/or a product that acts on the synthesis of collagen, in particular collagen and precursors thereof, such as procollagen type I, elastin, hyaluronic acid, vitamin C, alpha-lipoic acid, and cosmetically acceptable derivatives thereof.

By way of products that act on fibronectin synthesis, mention will be made of galactolipids, in particular monogalactosylmonoglycerides (MGMGs), monogalactosyldiglycerides (MGDGs), digalactosylmonoglycerides (DGMGs) and digalactosyldiglycerides (DGDGs). Mono- or digalactosyldiglycerides will advantageously be chosen.

By way of products that act on elastin synthesis, mention will be made of vitamin C.

The composition may also advantageously contain a product that acts on the microcirculation, in particular an extract of cinnamon, an extract of *Ginkgo biloba* or an extract of dew grass.

The invention also relates to a cosmetic care method for modifying the surface of the skin by giving it a smoother appearance through a reduction in the depth of wrinkles and fine lines and/or by providing it with a re-plumping effect. This method comprises the application, to the areas of skin in question, of a cosmetic composition as defined above.

Other features and advantages of the invention will become apparent on reading the examples which follow and which are given purely by way of illustration.

EXAMPLES

Example I

Preparation of Extracts According to the Invention

1a. Extraction with Supercritical $CO_2$ in the Presence of 3% Ethanol 60 g of exudate consisting of half resin and half sawdust are treated by extraction with supercritical $CO_2$ with 2.8% of ethanol at 60° C. and at 290 bars, using the apparatus referenced Separex model SF500. After decompression of the $CO_2$ from the supercritical state to the gas state, an ethanolic extract is obtained which is subsequently subjected to a vacuum-evaporation step in order to remove the ethanol.

The extract thus obtained is in the form of an orangey paste.

This extract, noted extract I, is subsequently solubilized at 5% weight by volume in DMSO so as to prepare a stock solution for the biological tests.

1b. Preparation of an Extract by Extraction with Methoxynonafluorobutane 100 g of the same starting material as in example 1.a are treated with 500 ml of methoxynonafluorobutane (HFE 7100) with magnetic stirring at reflux (67° C.). The extraction time is 3 h, the suspension obtained is filtered under reduced pressure. The filtrate is evaporated in a rotary evaporator at 40° C.

The extract, noted II, is dissolved at 5% weight by volume in DMSO so as to prepare a stock solution for the biological tests.

1.c Preparation of an Extract Using Ethoxynonafluorobutane as Extraction Solvent The procedure is carried out as in example 1.b, but using another fluorinated solvent, ethoxynonafluorobutane.

100 g of starting material are extracted with 500 ml of solvent (HFE 7200) with magnetic stirring at reflux at 76° C.

The extraction time is 3 h. The suspension obtained is filtered under reduced pressure.

The filtrate is evaporated in a rotary evaporator at 40° C.

The extract, noted III, is dissolved at 5% weight by volume in DMSO so as to prepare a stock solution for the biological tests.

1.d Preparation of an Extract Using 1,1,1,3,3-pentafluorobutane as Extraction Solvent 100 g of the same starting material as in the previous examples are treated with 500 ml of solvent with magnetic stirring at reflux (at 40° C.).

The extraction time is 3 h.

The suspension obtained is filtered under reduced pressure.

The filtrate is evaporated in a rotary evaporator at ambient temperature.

The extract, noted IV, is dissolved at 5% weight by volume in DMSO so as to prepare a stock solution for the biological tests.

1.e Preparation of a Purified Extract Rich in Cadalene

In a first step, 76 g of the same starting mixture of resin and sawdust are treated under the conditions described in example 1.a.

Approximately 10 g of a first extract, still in the form of an orangey paste, are then obtained.

In a second step, 8.81 g of this first extract are subsequently fractionated by flash chromatography on a silica gel consisting of heptane and silica (polar stationary phase with a 70-230 mesh porosity).

Various mixtures of heptane and diethyl ether are prepared so as to create a solvent gradient of increasing polarity, and they are used to obtain various fractions pushed by a stream of nitrogen.

Table 1 below gives the results of the fractionation.

TABLE 1

| Elution | Solvent | Volume used (in ml) | Fraction | Weight recovered (in g) |
|---|---|---|---|---|
| 1 | Heptane | 730 | F1 | 0.005 |
|   |   |   | F2 | 0.00104 |
| 2 | Heptane/Ether 90/10 (v/v) | 730 | F3 | 0.01556 |
|   |   |   | F4 | 0 |
| 3 | Heptane/Ether 80/20 (v/v) | 730 | F5 | 0.45627 |
|   |   |   | F6 | 1.71078 |
| 4 | Heptane/Ether 70/30 (v/v) | 730 | F7 | 1.6124 |
|   |   |   | F8 | 0.9976 |
| 5 | MeOH | 730 | F9 | 3.4556 |

Each fraction thus obtained is analyzed by HPLC with double UV-detection at 210 nm and 230 nm.

Fraction F5 comprises the desired cadalene. The latter is therefore subsequently purified in a third step by preparative high performance liquid chromatography (Shimadzu apparatus) under the following conditions:

reverse-polarity stationary phase: Lichrospher 100 RP 18 column (LXI: 250×25 mm, diameter: 5 μm).

Mobile phase with an elution gradient consisting of water/acetonitrile mixtures (see Table 2 below),

TABLE 2

| Time (min) | % acetonitrile |
|---|---|
| 0 | 70 |
| 25 | 95 |

Flow rate: 20 ml/min.

UV detection at 230 nm.

Injection: of 124 mg of fraction 5 dissolved in 2 ml of acetonitrile.

The cadalene peak emerges at 20.1 min. The recovered phase is evaporated in a rotary evaporator under reduced pressure. 7.7 mg of cadalene (in the form of an oil) with a purity of 95% (estimated by HPLC at 210 nm) are recovered.

The extract, noted V, is dissolved at 2.75% (w/v) in DMSO so as to prepare a stock solution for the biological tests.

Example 2

Demonstration of the Action of the Extracts of the Invention on Lipogenesis

The cells used are normal human pre-adipocytes (source R&D biotech).

Cells that are confluent initially cease to divide so as to enter into their early differentiation phase. This differentiation results in the formation of colonies of cells which undergo adipocyte conversion.

This differentiation is accompanied by changes in the biosynthesis of several proteins, and in an increase in various enzyme activities, including glycerol-3-phosphate dehydrogenase, known as $G_3PDH$.

It is remembered that $G_3PDH$ allows the formation of glycerol-3-phosphate, a molecule subsequently involved in the neosynthesis of intracellular lipids (triglycerides). Thus, an increase in the activity of $G_3PDH$ is directly linked to the reinforcement of this synthesis.

We tested the effect of extracts of *Daniellia oliveri* according to the invention, on this model.

1—Products Used

The positive control used for increasing lipogenesis is Pulpactyl® sold by the company Silab. It is a sterile aqueous solution of butylene glycol and of *Artemisia abrotanum*. The Pulpactyl® is used at the concentration of 0.5% directly in the culture medium.

Extracts I to V of *Daniellia oliveri* according to the invention are dissolved in DMSO in such a way that they are all tested at the same concentration of 25 mg/ml. The extracts according to the invention are introduced into the culture medium at 0.1% v/v, i.e. final concentrations of active agent of 25 μg/ml. In parallel, an excipient control (DMSO) at a final concentration of 0.1% v/v was prepared.

2—Culture Protocol

The cells used are normal human pre-adipocytes (source R&D biotech).

The pre-adipocytes are seeded at the bottom of 12 well culture microplates, with Preadipocyte Growth Medium, until confluence. During the differentiation phase, the cells are cultured in the presence of Preadipocyte Differentiation Medium (supplied by R&D biotech) supplemented with bovine insulin (0.5 μg/ml), dexamethasone (400 ng/ml) and IBMX (44 μg/ml) or 3-isobutyl-1-methylxanthine sold by A. G. Scientific Inc.

During the phase of treatment with the extracts according to the invention, Adipocyte Nutrition Medium, which no longer contains insulin, but 3% fetal calf serum (FCS), is used.

The extracts according to the invention are tested in triplicate.

The culturing operations are carried out in the following way:

At day D=0: seeding at a rate of 5000 cells/cm$^2$ in Preadipocyte Growth Medium.

At D=2 and D=4: medium change.

At D=6: culturing with Preadipocyte Differentiation Medium for 3 days.

From D=9 to D=18: culturing with Adipocyte Nutrition Medium.

At D=18: medium replaced with Adipocyte Nutrition Medium containing 25 µg/ml of a test extract according to the invention.

Treatment repeated 24 hours later.

After 48 hours of treatment, culture medium removed and cells ground for assaying the $G_3PDH$ activity.

3—Assaying of $G_3PDH$ Activity 3-1 Recovering the Cell Lysate

After the culture medium has been removed by suction, 500 µl per well of lysis buffer (25 mM Tris, 1 mM EDTA, pH 7.5) are added. After the cells have been scraped and recovered in an Eppendorf tube, they are centrifuged for 5 minutes at 6000 g in order to be able to remove the supernatant. The latter is frozen at −20° C. for subsequent assaying of the $G_3PDH$ activity and of the proteins.

3-2 Assaying of the $G_3PDH$ Activity 3-2.1 Principle

The cell monolayer is recovered by scraping and is vigorously homogenized in TRIS-HCl buffer (25 mM, pH 7.4) containing 1 mmol EDTA at 4° C. The assaying of the $G_3PDH$ activity is carried out on the supernatant of the ground cellular material immediately after centrifugation.

$G_3PDH$ catalyzes the following reaction:

Dihydroxyacetone phospate → Glycerol-3-phosphate
NADH    $NAD^+$

For each product tested, the conversion of the coenzyme NADH (hydrogenated nicotinamide adenine dinucleotide) to NAD, which reflects the rate of the enzyme reaction, and therefore the activity of the $G_3PDH$ enzyme, is measured by spectrophotometry at 340 nm after one minute.

An absorption difference (ΔAbs)/min, which corresponds to the initial rate of the enzyme reaction between t=0 and t=1 min, can be calculated.

The total amount of cell proteins is evaluated by the BCA-PIERCE method: protein assay reagent.

3-2.2 Reaction Medium 1.5 mM NADH (Sigma, N7410): 50 µl of a solution at 2 mg/1.925 ml of assay buffer (50 mM triethanolamine, 1 mM EDTA, pH 7.5).

1 mM dihydroxyacetone (Sigma, D 7137): 50 µl of a solution at 3.6 mg/2 ml of assay buffer (50 mM triethanolamine, 1 mM EDTA, pH 7.5).

Assay buffer: 350 µl

Ground cellular material: 50 µl.

3-2.3 Results—$G_3PDH$ Activity

The results are given in Table 4 below, in which the $G_3PDH$ activity is expressed as a percentage. This value is obtained by comparing the value of Δabsorbance of the extract according to the invention with that of the excipient control supposed to represent the basal activity of the cells (i.e. an activity of 100%).

TABLE 4

| Extract | Dose µg/µL | % Activity |
|---------|------------|------------|
| I       | 25         | 240        |
| II      | 25         | 169        |
| III     | 25         | 242        |
| IV      | 25         | 213        |
| V       | 25         | 119        |
|         | 5          | 207        |
|         | 0.5        | 278        |

It clearly emerges from the table above that the products according to the invention very greatly increase the activity of the $G_3PDH$ enzyme in the normal human adipocyte cultures, compared with the activity of this enzyme in the control cultures. Thus, it is demonstrated that the products according to the invention contribute to substantially increasing the synthesis of intracellular lipids (triglycerides).

Example 3

Cosmetic Compositions According to the Invention

The proportions of the constituents below are expressed as percentages by weight relative to the final composition.

| Gel | |
|---|---|
| Glycol | 3 |
| AMPS polymer (Sepigel 305) | 3 |
| Hydrogenated castor oil (Cremophor CO-60) | 2 |
| Polyethylene glycol | 1.5 |
| Preservative | 0.5 |
| Fragrance concentrate | 0.3 |
| Water | 83.7 |
| Extract I | 5 |
| Benzophenone 4 | 1 |
| Cream | |
| Steareth-21 (Brij 721) | 2.5 |
| Glyceryl stearate (Tegin) | 1.1 |
| Stearyl alcohol | 5 |
| Glycerol tricaprate/caprylate | 11.5 |
| Butylene glycol | 3 |
| Glycerin | 2 |
| Preservative | 0.5 |
| Fragrance concentrate | 0.5 |
| Water | 64.4 |
| Extract III | 2 |
| Octyl methoxycinnamate | 7.5 |
| Lotion | |
| Butylene glycol | 3 |
| EDTA | 0.1 |
| Solubilizing agent | 1 |
| Fragrance concentrate | 0.3 |
| Alcohol | 5 |
| Water | qs |
| Extract IV | 0.05 |
| Benzophenone 4 | 0.13 |
| Re-plumping lipstick | |
| Lanolin | 8 |
| Polybutene | 10 |
| Parleam | 12 |
| Isostearyl isostearate | 15 |
| Pentaerythrityl tetraisostearate | 15 |
| Candelilla wax | 5 |
| Ozokerite | 1.5 |
| Beeswax | 2 |
| Polyethylene | 6 |
| Pigments | 5 |
| Pearlescent agents | 3 |

| | |
|---|---|
| Extract V | 0.5 |
| Castor oil | qs |

What is claimed is:

1. A method of cosmetic care for modifying the surface of the skin by giving the skin a smoother appearance through the reduction of the depth of wrinkles and fine lines and/or by providing the skin with a re-plumping effect, comprising: applying to parts of a subject's skin in need thereof, an effective amount of a cosmetic composition that comprises an extract of an exudate of the plant *Daniellia oliveri*, said exudate being at least partially made up of an oleoresin of said plant.

2. The method according to claim 1, wherein said exudate is a natural exudate of the plant *Daniellia oliveri* containing a mixture of oleoresin and of sawdust from wood and/or bark.

3. The method according to claim 1, wherein said extract is obtained by extracting said exudate with an apolar solvent.

4. The method according to claim 3, wherein said apolar solvent has a polarity parameter P' of between −2 and 0.2.

5. The method according to claim 3, wherein said apolar solvent is selected from the group consisting of fluoroalkanes, cyclohexane, cycloheptane, heptane, isoheptane, hexane and pentane, and mixtures thereof.

6. The method according to claim 3, wherein said apolar solvent is used in the presence of a polar solvent or a mixture of polar solvents.

7. The method according to claim 1, wherein said extract is obtained by extracting said exudate with $CO_2$ in the supercritical state, acting as an apolar solvent.

8. The method according to claim 7, wherein said apolar solvent is used in the presence of a polar solvent or a mixture of polar solvents.

9. The method according to claim 1, wherein said extract contains cadalene or 1,6-dimethyl-4-(1-methylethyl)naphthalene.

10. The method according to claim 9, wherein said extract is enriched in cadalene by means of at least one purification step.

11. The method according to claim 1, wherein said cosmetic composition contains from 0.01% to 5% by weight of said dry extract.

12. The method according to claim 1, wherein said cosmetic composition is formulated for topical application and is in the form of a lotion, a milk, a gel, a cream or a stick.

* * * * *